United States Patent [19]

Delius

[11] Patent Number: 5,538,694
[45] Date of Patent: Jul. 23, 1996

[54] DEVICE FOR SIMULTANEOUSLY OR SEQUENTIALLY CARRYING OUT CHEMICAL REACTIONS

[75] Inventor: Hajo Delius, Dossenheim, Germany

[73] Assignee: Deutsches Krebsforschungszentrum Stiftung Des Oeffentlichen Rechts, Heidelberg, Germany

[21] Appl. No.: 295,728

[22] PCT Filed: Feb. 27, 1993

[86] PCT No.: PCT/EP93/00457

§ 371 Date: Aug. 31, 1994

§ 102(e) Date: Aug. 31, 1994

[87] PCT Pub. No.: WO93/17785

PCT Pub. Date: Sep. 16, 1993

[30] Foreign Application Priority Data

Mar. 2, 1992 [DE] Germany ............... 42 06 488.0

[51] Int. Cl.$^6$ ....................................... B01J 8/00
[52] U.S. Cl. .................. 422/131; 422/196; 935/88
[58] Field of Search ................... 422/111, 116, 422/131, 134, 149, 196, 236, 237; 935/88

[56] References Cited

U.S. PATENT DOCUMENTS

| | | | |
|---|---|---|---|
| 4,728,502 | 3/1988 | Hamill | 935/88 |
| 4,744,037 | 5/1988 | Niina et al. | 364/497 |
| 5,137,698 | 8/1992 | Ansorge et al. | |

FOREIGN PATENT DOCUMENTS

| | | |
|---|---|---|
| 0164206 | 12/1985 | European Pat. Off. |
| 0181491 | 5/1986 | European Pat. Off. |
| 3525678 | 1/1986 | Germany |
| 3813671 | 11/1989 | Germany |
| 89/10188 | 11/1989 | WIPO |

Primary Examiner—Timothy M. McMahon
Assistant Examiner—Robert Carpenter
Attorney, Agent, or Firm—Spencer & Frank

[57] ABSTRACT

A device for simultaneously or sequentially carrying out chemical reactions includes a stack of four rods; and a carrier plate which is displaceable. The stack of four rods is composed of a first rod which has a position which is fixed and which has a plurality of throughgoing bores defined therein; a second rod which is in contact with the first rod, which is fixedly connected to the carrier plate so that the second rod is displaceable, and which has a throughgoing bore defined therethrough; a third rod which is in contact with the second rod, which is disposed so that it is displaceable by the carrier plate, arid which has defined therein a plurality of reaction chambers which are provided with two openings located opposite one another and which are present in a number n; and a fourth rod which is in contact with the third rod, which is fixedly connected to the carrier plate, and which has a throughgoing bore defined therein. The openings of the reaction chambers of the third rod and the throughgoing bores of all least one of the first, second, and fourth rods are positionable so that a plurality of positions are provided by means of displacing the rods with respect to one another in which a throughgoing connection is produced which extends through the stack of rods and comprises a reaction chamber and at least one throughgoing bore of the first, second and fourth rods.

15 Claims, 2 Drawing Sheets

5,538,694

1

DEVICE FOR SIMULTANEOUSLY OR SEQUENTIALLY CARRYING OUT CHEMICAL REACTIONS

BACKGROUND OF THE INVENTION

1. Field of the Invention

The invention relates to a device for simultaneously or sequentially carrying out chemical reactions.

2. Description of the Related Art

In many series of chemical experiments, it is necessary to bring a number of reaction partners to reaction with a predetermined substance and evaluate, further process or analyze the respective reaction products. In other series of chemical experiments, it is necessary to bring a predetermined substance into contact successively with a series of reagents and evaluate, further process or analyze the respective reaction products. Such series of experiments are always time-consuming and represent monotonous, routine work. Therefore, one tries to automate such series of experiments with the aid of suitable devices or apparatuses.

Particularly in biochemistry, such series of experiments, especially of the second type, must be performed frequently. An example of this is oligonucleotide synthesis, which has achieved great: significance for a number of molecular biology techniques. Particularly worth mentioning are the methods of PCR poly chain reaction) and DNA sequence analysis, in which so-called "primers," which are short, individual strands of DNA having a length of approximately 16 to 20 nucleotides, are used.

A further problem is that the substances and their reactions are often very expensive. Therefore, one will attempt to make do with the smallest possible quantities.

Particularly in sequence analysis with so-called "primer walking" methods, in which the primer sequence for the next sequencing step is read out of the newly-determined sequence and used for synthesis of a new primer, only very small quantities of oligonucleotides, approximately in the pMol range, are used for the actual determination of sequence.

There are numerous commercially-available apparatuses with which syntheses can principally be performed in series of experiments of the first or second type, and particularly oligonucleotide syntheses. However, all of these apparatuses are designed for substance quantities of more than 40 nMol, that is, for quantities that are more than 1000 times larger than needed. In many cases the high price of primer syntheses prevents widespread application of these methods with the known, commercially-available apparatuses. Moreover, the commercially-available apparatuses are designed for a maximum of four parallel syntheses, so that a large number of parallel syntheses, as required for primer-walking sequencing, for example, can only be performed in small work segments, with reloading of the apparatus during the work time, but not, for example, overnight.

From DE 38 13 671 A1 device of the type mentioned at the outset is known, which comprises a stack of superposed reaction plates that can be displaced selectively and incrementally relative to one another, and are provided with passages disposed linearly with incremental spacing, of which one is respectively configured as a reaction chamber. A vertically and a horizontally traveling plate-adjusting device serves in selective displacement of the respective plate relative to the rest of the plate stack. The liquid-tight seal is effected by means of O-rings which encompass the passages and are placed in grooves. Each plate includes a single reaction chamber; for n reactions to be carried out, (n+2) plates are necessary.

Because of the condition that a plate must be provided for each reaction chamber, the device becomes unnecessarily complicated, because each individual plate, with the exception of the first (bottommost) and the last (topmost), must be displaced separately. Hence, an expensive displacement device is required. Because the reagents must be conducted through the entire plate stack, a considerable stagnant volume results, particularly when many reactions are supposed to be carried out, and therefore many plates are required.

Corresponding devices that have rotating plates are known from EP 0 164 206 B1 and EP 0 181 491 A1.

Therefore, it is the object of the invention to propose a simpler device with the aid of which in principle a virtually unlimited number of chemical reactions of the type of series of experiments mentioned above can be carried out simultaneously or sequentially. In comparison to the known apparatuses, the device should be able to be operated with smaller substance quantities. Moreover, the device is intended to be designed such that it can be controlled automatically.

SUMMARY OF THE INVENTION

The object is accomplished by a device that has the features cited in the characterization of the first claim. Advantageous embodiments of the device of the invention are disclosed in the dependent claims.

The invention is based on the following considerations:

When the consumption of reagents is supposed to be kept low, the volume of the reaction chambers and the stagnant volume between valves via which the reagents are routed into the reaction chambers, and the reaction chambers must be kept as small as possible.

In the commercially-available devices the switching valves are connected to the reaction chambers via PTFE hoses. Although the reaction chambers only have a volume of approximately 100 µl, the total free volume is approximately 200 µl. In the device of the type mentioned at the outset, the reagents must be conducted through a stack of numerous plates.

Furthermore, when the times for a synthesis for small quantities are also supposed to be kept short, it must be possible to keep the concentration of the reagents high despite the small required quantities.

The conventional arrangement of standard switching valves and reaction chambers, or of stacks of numerous plates, are an obstacle to meeting both requirements.

Therefore, a device is proposed which does not use valves and in which only four plates or rods are required. In this way the stagnant volume can be significantly decreased.

BRIEF DESCRIPTION OF THE DRAWINGS

Further advantages and features of the invention will become apparent from the detailed description below taken from the drawings in which.

DESCRIPTION OF THE PREFERRED EMBODIMENTS

Figure 1:
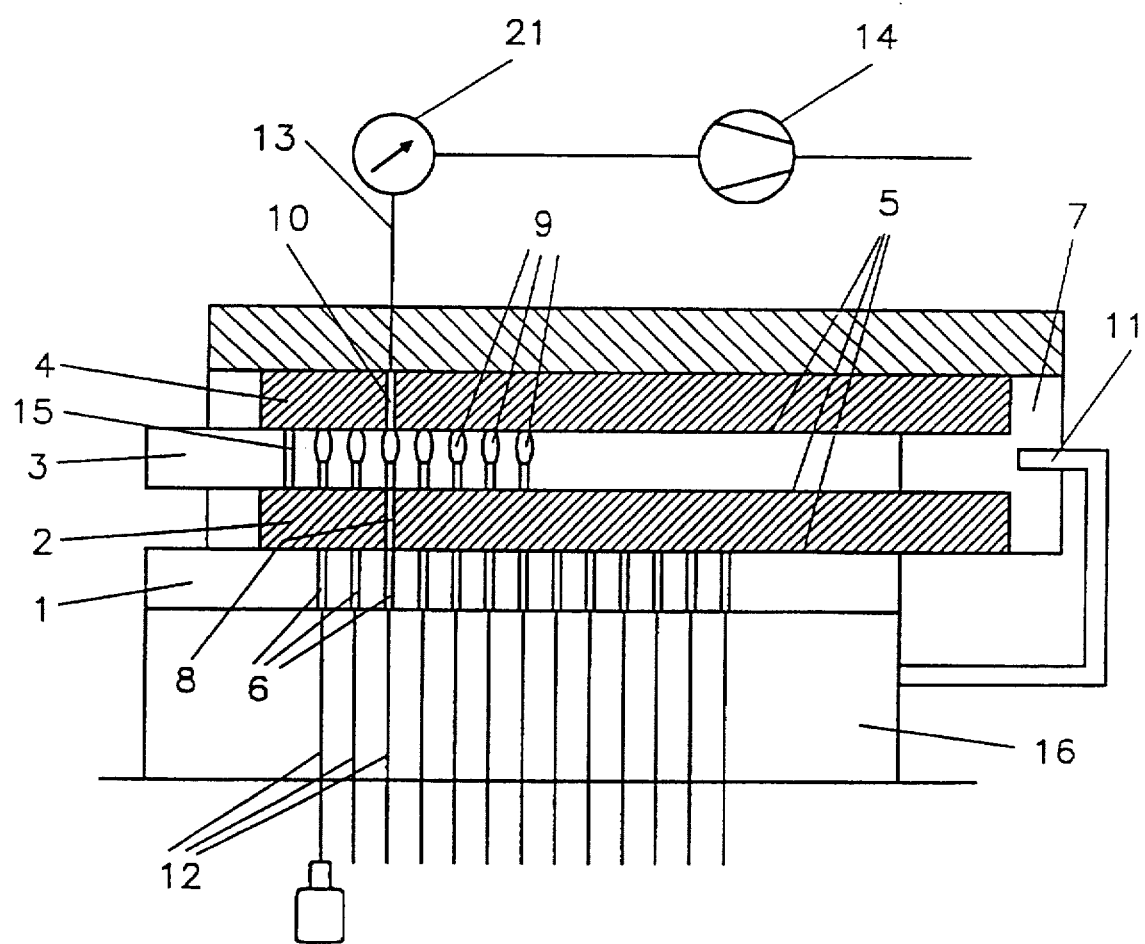
FIG. 1 shows an embodiment of the device according to the invention in which provided substances can be brought into contact with respectively one reaction partner in accordance with the first type of the series of experiments mentioned at the outset. As is described below regarding this figure.

The terms "below" and "above" are used below solely in the interest of a clear representation of the invention, and relate to the embodiments shown in the figures. The device shown in, for example, FIG. 1 can also be operated inverted, however ("standing on its head") or lying on its side. The invention also encompasses such embodiments.

The device according to the invention essentially comprises four rods 1, 2, 3, 4, which are disposed horizontally and are superposed. The rods thus touch six surfaces 5, which will be referred to hereinafter as contact surfaces. The contact surfaces are preferably machined to be planar, so that they effect a liquid-tight seal without additional sealing means, such as O-rings. The upper 4 and lower rod 1 respectively touch the adjacent rod by way of a contact surface 5; the two center rods 2, 3 each have two contact surfaces. The contact surfaces 5 should be as even and smooth as possible in order to be able to effect the mentioned liquid-tight seal; they are machined by means of, for example, grinding and polishing in such a way that they can be moved relative to one another gap-free.

The contact surfaces are pressed against each other in the device according to the invention. The required pressing pressure can be applied by utilizing the dead weight of the rods and/or by means of spring elements. The magnitude of the pressing pressure is a function of, among others, the working pressure of the device, the viscosity of the reagents used and the material of the rods, and particularly of the surface tension of the reagents on the material, and is preset as a function of these parameters.

With this arrangement it is accomplished that the rods can be moved relative to one another at their contact surfaces, and that the contact surfaces nevertheless form a liquid block and thus effect a liquid-tight seal without additional auxiliary means.

In addition, the shape of the rods can be freely selected. One will preferably use rectangular or plate-shaped rods. Furthermore, on the sides that are not used as contact surfaces, the rods can be provided with guide grooves or guide rails, spring elements and such holding elements that permit an exchange.

The bottommost, first rod 1 is fixedly connected with the device. For example, the first rod can be secured on a base plate 16. It further includes a plurality of throughgoing bores 6. Although the bores need not extend essentially vertically, for reasons of production technology one will dispose the bores perpendicular to the longitudinal axis of the rods. Liquid-tight reagent lines 12 which terminate in, for example, reagent supply bottles, are connected from below to the bores, for example, by means of inserted fittings. The number of bores 6 is a function of the number of reagents necessary for the series of experiments. One will select the number of bores such that, if possible, a bore and hence a reagent line are available for each required reagent, so that the supply bottles need not be exchanged during the experiment.

The second rod 2, which is located above the first rod 1 and touches it by way of the two respective contact surfaces 5, is fixedly connected to a carrier plate 7 and can be displaced relative to the first rod by means of a horizontal movement of the carrier plate. This rod has a throughgoing, preferably vertically-disposed bore 8.

The third rod 3, which is located above the second rod 2 and touches it by way of the two contiguous contact surfaces, is likewise connected to the carrier plate 7, but in such a way that it can be displaced relative to the carrier plate. It has a number n of reaction chambers 9, which are open to the top and bottom. The shape of the reaction chambers depends on the type of reaction to be carried out, and the quantity of reagents. In principle, the reaction chambers can be created by bores. Plastic frits, between which a carrier of porous glass is held, are frequently used as reaction chambers in oligonucleotide syntheses. Paper in the form of a roll or the form of stacked or folded layers can be used as the carrier. In this instance it can be necessary that the reaction chambers be expanded to bulge, as indicated in the figure. The third rod 3 can then comprise, for example, two layers, of which one includes the reaction chambers and the lower openings, and the other is configured as a lid with the corresponding upper openings. Although the openings of the reaction chamber, which are located opposite one another, need not be disposed essentially vertically one above the other, such an arrangement is preferred for reasons of production technology. The number n of reaction chambers in the third rod 3 is a function of the number of reactions to be carried out, and can—with a corresponding length of the rod—be selected freely in principle.

It proves advantageous when all of the rods, or at least the third rod 3, can be tempered and thermostatted. In this case reactions can also be carried out at a predetermined temperature above or below ambient temperature.

The fourth rod 4, which is located above the third rod 3 and touches it by way of the two contiguous contact surfaces, is, like the second rod 2, fixedly connected to the carrier plate 7, and includes a throughgoing bore 10. A vertical arrangement is again preferred for this bore.

For the function of the device, it is essential that n different positions exist for the rods 2, 3 and 4, in which the bores 8 and 10 and the upper and lower openings of one of the reaction chambers represent a throughgoing connection. The number n corresponds to the number of reaction chambers provided. This condition is most simply met when the bores 8 and 10 are configured vertically and lie on a common straight line, and the opposite openings of each reaction chamber are disposed vertically one above the other. In principle, however, the bores 8 and 10 can also be disposed at other angles, and the upper and lower openings of each reaction chamber can be offset relative to one another, provided that the named condition is met.

The bore 10 of the fourth rod 4 can be connected, for example, by way of suitable fittings, to a line 13, into which a pump 14 is inserted. A pump is necessary in particular when the reagent lines 12, which terminate in the lower part of the bores 6, and the reagent supply bottles connected thereto are net disposed in such a way that the reagents flow into the device due to a gradient. Furthermore, a pump can be omitted when the device is operated "standing on its head," conversely to the embodiment illustrated in the figure, so that the first rod 1 represents the upper rod and the fourth rod 4 represents the lower rod. In these cases a pump can be omitted in many applications of the device according to the invention.

In general, a suction pump is used for the embodiment illustrated in the figure. A pump in which the conveying direction can be reversed, for example a hose pump, is particularly preferred. By means of a periodic reversal of the conveying direction, a good thorough mixing of the reagents in the reaction chambers 9 can be reached. In addition to the pump 14, a flow monitor 21 can be integrated into the line.

For automatic operation of the device according to the invention, it is extremely advantageous when both the bores 6 in the first rod 1 and the upper and lower openings of the reaction chambers 9 in the third rod 3 are disposed at a constant distance. In this case the carrier plate 7 can be moved horizontally by a stepping motor, e.g., automatically controlled by a corresponding computer, where the steps of the stepping motor correspond to the constant distance, and the respective duration of a position is predetermined by the computer. The pump can also be actuated by means of a stepping motor and the computer.

The third rod 3, which includes the reaction chambers 9, is moved relative to the carrier plate 7 during operation of the device. This movement can be accomplished with different structural elements. For example, a further stepping motor is provided for the horizontal movement of the third rod 3. This stepping motor can also be controlled by a computer. However, it often appears simpler to provide a stop 11 (FIG. 1) or two stops 11, 11' (FIG. 2) to assure that, when the carrier plate 7 is moving, the third rod 3 is held at least intermittently in a stationary position relative to the moving carrier plate 7. If the third rod 3 does not impact upon the stop, it is moved together with the carrier plate due to the friction of the contact surfaces.

In principle, the stop can also be designed to be adjusted, for example, mechanically by means of a screw thread, or automatically by means of a motor and a computer. The way in which the stop 11 is disposed depends on whether the first or second type of series of experiments mentioned at the outset is to be carried out.

In FIG. 1 the stop 11 is disposed on the right side of the figure, and causes the reaction chambers 9 of the third rod 3 to be held stationary relative to the first rod 1 and the base plate when the carrier plate 7 is moving to the right. In this way the reaction chambers 9 can be positioned one behind the other between the bores 8 and 10 in the rods 2 or 4, in order to permit a reagent flow through the selected reaction chamber via the reagent lines 12 following the displacement of the carrier plate 7 to the left.

In addition to the reaction chambers 9, the third rod 3 preferably includes a bore 15, which is disposed laterally next to the group of reaction chambers, with the bore 15 being disposed in such a way that its distance from the upper and lower openings of the closest reaction chamber corresponds to the above-mentioned constant distance. The device can be rinsed with this bore 15. Moreover, the lines 12 and 13 can be deventilated by way of this bore.

The diameter of all of the bores should match the type of reagent, the synthesis quantities to be used and the desired flow, as well as the tolerable flow resistance, because the stagnant volume increases with the diameter. In principle, however, there are no limitations with regard to the diameter.

In principle, all materials that can be pressed or machined to an accurate size, as well as bored, milled and ground, can be used for the rods of the device according to the invention, and particularly for the contact surfaces 5. The rods can be produced from a metal or a plastic, e.g., by means of injection-molding. Limitations can arise with respect to the reagents to be used, against which at least the bores 6, 8, 10 and the reaction chambers 9 and the contact surfaces 5 must be resistant. For the rods, for example, a special steel or aluminum can be used, in which case one will specially treat or coat the contact surfaces, if need be. A very well-suited material for the rods is so-called "machinable glass," a mixture of glass and mica that can be sawed, milled, bored and ground with high precision. This material, which is resistant to most aggressive reagents, is sold by Corning, USA under the brand name of, for example, MACOR.

The rods need not be made of the same material. For example, a third rod of steel and aluminum can be combined with MACOR$^R$ rods.

In comparison to the known devices, the device according to the invention has numerous essential advantages.

The tightness of ground contact surfaces between the rods is generally entirely sufficient for extracting the reagents from lower-lying reagent supply bottles, and good enough to keep cross-contamination of the reagents sufficiently low. If the contact surfaces are kept free from scratches, it is to be expected that the durability of the device according to the invention is better than the durability of conventional PTFE/ steel valves in the known devices.

A further advantage is that the stagnant volume can be kept very small, e.g., at approximately 10 µl. This is accomplished in that the number of necessary rods is significantly reduced in comparison to the device of the type mentioned at the outset with the same number of reaction chambers.

The reaction chambers can be rinsed with very low volumes of reagents, and the reagents are brought to the reaction chambers with only slight mixing. The use of reagents can therefore be optimally adapted to small synthesis quantities. For example, oligonucleotide syntheses could be carried out with a prototype of the device of the invention with carrier material for approximately 10 nMol, with a total throughput of reagents of only 1.7 ml per coupling; this is approximately 4 to 5 times less than in known devices.

The device according to the invention can also be adapted in numerous embodiments to the object to be accomplished. Thus, the number of reaction chambers and reagent lines can be virtually freely selected with correspondingly long rods. The reaction chambers and the bores for the reagent lines can also be disposed in parallel rows, in which case the carrier plate is not moved horizontally only in one direction (x-axis), but in two directions (x—and y-axis). In this instance, it can be advantageous when the second 2 and the fourth 4 rods include not only one, but a plurality of bores, of which respectively one is located above the parallel rows of the reaction chambers and the bores for the reaction chambers.

The invention and its mode of operation are explained in detail below by way of a process embodiment.

EXAMPLE

Embodiment for Oligonucleotide Synthesis

Figure 2:
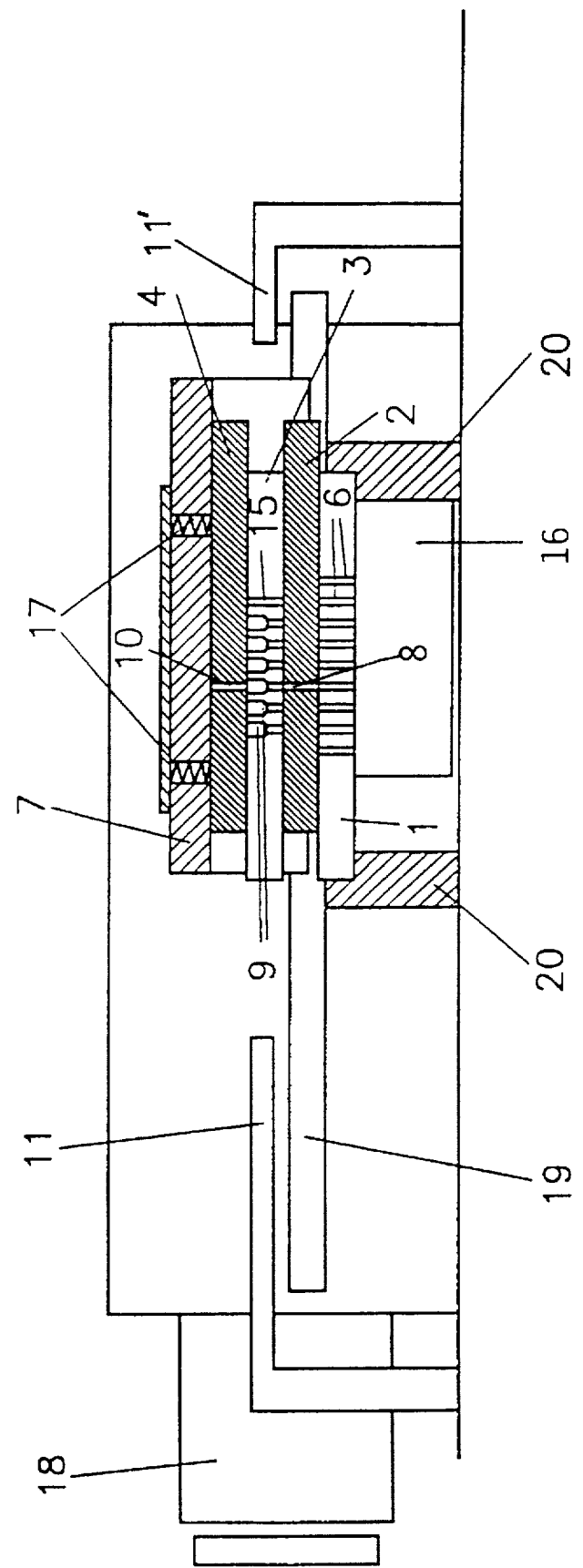
FIG. 2 represents a further embodiment in which oligonucleotide synthesis is performed.

The embodiment used for oligonucleotide synthesis is illustrated in FIG. 2; it included seven reaction chambers 9 and 14 bores 6 in the first rod, which were respectively disposed in a single row. All of the bores extended vertically. The carrier plate was moved via a spindle 19 by means of a stepping motor 18, which was controlled by a computer. A hose pump 14, which was likewise controlled by the computer, was inserted into the line 13 at bore 10 (FIG. 1). The efficiency of the synthesis was monitored by an absorption-flow monitor 21 (see FIG. 1) that was inserted into the line 13, between bore 10 and the hose pump 14.

The device further included two stops 11, 11'. The rod 1 was fixed on the base plate 16 with the blocks 20. These blocks are mounted in front of the displaceable carrier plate 7.

Performance of an Oligonucleotide Synthesis

Oligonucleotide syntheses were carried out with the embodiment of the device according to the invention, as described in Example 1.

The individual nucleotide building blocks were coupled to the first activated nucleotide in repeated synthesis cycles, the nucleotide being held between the plastic frits on the porous glass in a reaction chamber. These cycles consist of a) removing the trityl protective group by means of trichloroacetic acid dissolved in dichloro ethane, b) coupling of the nucleotide building block which was present as phosphoramidite in stabilized form in acetonitrile, c) blocking, by means of so-called capping, of the nucleotide ends that have not reacted, d) oxidation of the phosphorus with iodine.

A prerequisite for a synthesis of the oligonucleotides with good efficiency is the most extensive exclusion of moisture possible. This could be assured by the device used.

Preparation of a Synthesis

Springs 17 are released so that rod 4 can be raised and rod 3 can be removed from the apparatus. The column filling is brought into the reaction chambers 9. One frit (3.0 mm×1.5 mm, polyethylene) is pressed into each reaction chamber 9, followed by approximately 2–3 mg of a nucleoside-charged CPG carrier (Millipore, approximately 5 µmol/g, 500 Angstrom pores), and a second frit as a cover. The nucleoside carrier is selected for the appropriate reaction chamber (G, A, T or C) to correspond to the sequence to be synthesized.

After the apparatus has been turned on, the carrier plate 7 is moved to the left into a reference position. The rod 3, which is loaded with the column filling, is reinserted into the apparatus. The rod 4 is again placed on top, and the springs are tensioned in order to press the two rods 3 and 4 against the rod 2. In the prototype, the pressure is approximately 500 p, but is adapted according to the quality of the contact surfaces.

Under PC control, the carrier plate is moved to the right so that the right stop 11' displaces the rod 3 so far that bore 15 in rod 3 is aligned with bore 8 in rod 2 and bore 10 in rod 4.

Accordingly, the carrier plate can then be displaced back to the left, so that bore 8 in rod 2 comes to stand above the respective required reagent line 6.

To deventilate and rinse the reagent lines, predetermined quantities of all of the reagents are now pumped away through bores 8, 15 and 10 via the line 13 and the pump 14. The sequence is:

Dichloro ethane, trichloroacetic acid (TCA, 1% in dichloro ethane), dichloro ethane, acetonitrile, capping reagent A, capping reagent B, oxidation reagent, acetonitrile, tetrazol, A-amidite, T-amidite, C-amidite and G-amidite, acetonitrile, dichloro ethane.

Following this the apparatus is ready for oligonucleotide synthesis.

The sequences to be synthesized are entered via the PC keyboard. In this manner up to seven sequences having a length of up to 50 nucleotides can be entered on the prototype.

After entry, the synthesis is initiated from the PC. For synthesis of the finest oligonucleotide, the carrier plate is moved so far to the left that the rod 3 between the rods 2 and 4 is displaced to the right by the left stop until the first reaction chamber 9 in rod 3 is aligned with the bores 8 and 10 in the rods 2 and 4.

Beginning of a Synthesis

At the beginning of the synthesis, first the carrier plate is moved to the right again until the bore 8 stands above the reaction line for dichloro ethane. The reaction chamber 9, which contains the column filling, is washed with 140 µl of dichloro ethane. During the wash program, good thorough mixing is assured by a brief pump phase in the reverse direction.

Afterward the carrier plate is moved into the TCA position. The reaction chamber is rinsed thoroughly with TCA, by means of which the protective group on the nucleotide of the CPG material is removed. Afterward, washing with dichloro ethane takes place again.

Addition of a Nucleotide

1. Washing with acetonitrile. As in washing with dichloro ethane: 140 µl with brief pump reversal.

2. Addition of amidite solution and tetrazol, the activator. For better thorough mixing, 10 µl tetrazol and 10 µl amidire solution are alternatingly pumped into the reaction chamber three times, followed by 10 µl tetrazol. The carrier plate is moved into the acetonitrile position for the reaction. For further thorough mixing, in this position 10 µl of the reaction mixture are pumped back and forth in the reaction chamber three times at a low pumping speed. After completion of the reaction, washing with acetonitrile takes place.

3. To inactivate the free groups that have not coupled amidite, the reagents capping A and capping B are pumped into the reaction chamber and mixed briefly.

4. After brief washing with acetonitrile, oxidation reagent is pumped through the chamber.

5. After one more washing with acetonitrile, followed by dichloro ethane, the trityl protective group is split from the newly-joined amidite with TCA. The quantity of this trityl residue can be determined in the flow monitor by means of absorption measurement at a wavelength of 550 nm.

The coupling of a nucleotide is completed with this step. When a further nucleotide is to be added, steps 1 through 5 are followed.

After coupling of the last nucleotide of the entered oligonucleotide sequence, washing with dichloro ethane takes place.

In case a further oligonucleotide is to be synthesized, the carrier plate is displaced to the left until the rod 3 is displaced so far to the right by the left stop that the next reaction chamber is alined with the bores 8 and 10 in the rods 2 and 4. Then the synthesis of the next oligonucleotide is carried out as described above.

What is claimed is:

1. A device for one of simultaneously or sequentially carrying out chemical reactions, comprising:

a stack of four rods which has a longitudinal axis and in which the four rods are disposed on parallel and in sequentially stacked contact with one another, only one of which four rods includes reaction chambers defined therein, and three of which four rods are displaceable along the longitudinal axis of the stack; and a carrier plate which is displaceable along an axis which is parallel to the longitudinal axis of the stack, wherein the stack of four rods is comprised of:

a first rod which has a position which is fixed and which has a plurality of throughgoing bores defined therein;

a second rod which is in contact with the first rod, which is fixedly connected to the carrier plate so that the second rod is displaceable relative to the first rod, and which has a throughgoing bore defined therethrough;

a third rod which is in contact with the second rod, which is disposed so that it is displaceable by the carrier plate, and which has defined therein a plurality of reaction chambers which are provided with two openings located opposite one another and which are present in a number n; and a fourth rod which is in contact with the third rod, which is fixedly connected to the carrier plate, and which has a throughgoing bore defined therein, and wherein the openings of respective ones of the reaction chambers of the third rod and the throughgoing bores of at least one of the first, second, and fourth rods are positionable so that a plurality of positions are provided by means of displacing the rods with respect to one another in which a throughgoing connection is produced which extends through the stack of rods and comprises a reaction chamber of the third rod and at least one throughgoing bore of the first, second and fourth rods.

2. The device according to claim 1, wherein the third rod has a plurality of different positions having a number n relative to the second and fourth rods in which the throughgoing bores of the second and fourth rods and the openings of one of the reaction chambers of the third rod produce a throughgoing connection.

3. The device according to claim 1, wherein the third rod has defined therein a throughgoing bore.

4. The device according to claim 1, wherein the plurality of throughgoing bores defined in the first rod are spaced apart by a predetermined distance, wherein the respective openings of the reaction chambers in the third rod are spaced apart by a predetermined distance, and wherein the predetermined distance by which the plurality of throughgoing bores defined in the first rod are spaced apart and the predetermined distance by which the respective openings of the reaction chambers in the third rod are spaced apart are the same so that an alignment produces a throughgoing connection thereof respectively.

5. The device according to claim 4, wherein the third rod has defined therein a throughgoing bore which is disposed at a predetermined distance from the respective two openings located opposite one another of one of the reaction chambers of the third rod, and wherein the predetermined distance of the throughgoing bore of the third rod and the predetermined distance by which the openings of the reaction chambers in the third rod are spaced apart is the same.

6. The device according to claim 1, wherein the respective throughgoing bores of the second and the fourth rods extend perpendicular to the longitudinal axis of the stack and lie on a common straight line.

7. The device according to claim 1, further comprising a plurality of reagent lines, and wherein the plurality of throughgoing bores of the first rod are respectively connected in a liquid-tight manner with the plurality of reagent lines.

8. The device according to claim 1, further comprising a first stepping motor for moving the carrier plate along an axis which is parallel to the stack, and wherein the third rod is displaced by the carrier plate so that the throughgoing bores of the second and fourth rods are aligned with the two openings of one of the reaction chambers, the two openings being located opposite one another.

9. The device according to claim 8, further comprising a second stepping motor for moving the third rod along an axis which is parallel to the stack.

10. The device according to claim 9, wherein at least one of the first stepping motor and the second stepping motor are controlled by a computer.

11. The device according to claim 1, further comprising at least one stop, and wherein the third rod is displaced by the carrier plate and abuts one of the at least one stop so that the throughgoing bores of the second and fourth rods are aligned with the two openings of one of the reaction chambers, the two openings being located opposite one another.

12. The device according to claim 11, further comprising a second stepping motor for moving the third rod along an axis which is parallel to the stack.

13. The device according to claim 12, wherein the second stepping motor is controlled by a computer.

14. The device according to claim 1, wherein the four rods are made of a material selected from the group consisting of a metal, a plastic, and a machinable glass.

15. The device according to claim 14, wherein the four rods are in contact with a one another by way of contact surfaces that are machined to be planar and that effect a liquid-tight seal.

* * * * *